United States Patent
Sato et al.

(10) Patent No.: US 6,790,970 B2
(45) Date of Patent: Sep. 14, 2004

(54) (METH) ACRYLIC ACID ESTER COMPOUND

(75) Inventors: Kenichiro Sato, Shizuoka (JP); Toshiaki Aoai, Shizuoka (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/275,941

(22) Filed: Mar. 25, 1999

(65) Prior Publication Data

US 2002/0002295 A1 Jan. 3, 2002

(30) Foreign Application Priority Data

Mar. 26, 1998 (JP) .......................... 10-079454

(51) Int. Cl.⁷ .................. C07J 9/00; C07J 7/00
(52) U.S. Cl. ............ 552/553; 552/555; 552/609
(58) Field of Search ............. 552/609, 553, 552/555

(56) References Cited

PUBLICATIONS

Ahlheim et al, Radikalisch polymerisierbare Gallensauren in Monoaschichten, Mizellen and Vesikeln, Makromol. Chem. 193(3), pp. 779–797.*

Y.H. Zhang, X.X. Zhu, Polymers made from cholic acid derivatives: selected properties, Macromolecular Chemistry and Physics (1996), 11 pages.

* cited by examiner

*Primary Examiner*—Ba K. Trinh
*Assistant Examiner*—Taylor Victor Oh
(74) *Attorney, Agent, or Firm*—Sughrue Mion, PLLC

(57) ABSTRACT

The present invention provides a novel (meth)acrylic acid ester compound useful as a resin material for photosensitive compositions, which enables control of the molecular weight of a resin to be prepared. The novel (meth)acrylic acid ester compound is one represented by the following formula (I):

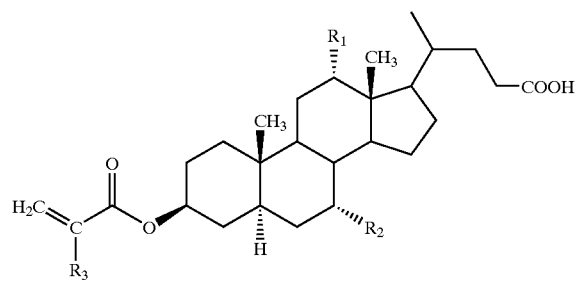

wherein $R_1$ and $R_2$ each independently represent a hydrogen atom or a hydroxyl group; and $R_3$ represents a hydrogen atom or a methyl group.

8 Claims, No Drawings

(METH) ACRYLIC ACID ESTER COMPOUND

FIELD OF THE INVENTION

The present invention relates to a novel (meth)acrylic acid ester compound. More particularly, the present invention relates to a monomer material for an alkali-soluble resin which can be preferably used as a photosensitive composition for use in the production of semiconductors such as IC, circuit boards such as liquid crystal and thermal head and printing plates and other photofabrication processes.

BACKGROUND OF THE INVENTION

As alkali-soluble resins to be incorporated in photosensitive compositions there have been studied various compounds.

For resins to be incorporated in positive-working photoresist compositions for exposure to ArF exima laser for the formation of circuit board for example, the use of a polymer having an alicyclic group has been extensively studied. Specific examples of such a polymer include those described in JP-A-4-39665 (The term "JP-A" as used herein means an "unexamined published Japanese patent application"), JP-A-5-80515, JP-A-5-265212, JP-A-5-297591, JP-A-5-346668, JP-A-6-289615, JP-A-6-324494, JP-A-7-49568, JP-A-7-185046, JP-A-7-191463, JP-A-7-199467, JP-A-7-234511, JP-A-7-252324, and JP-A-8-259626. In these publications, repeating units having various alicyclic groups are described.

Further, Makromol. Chem., Vol. 193, page 779 (1992) describes a methacrylic acid ester compound containing an alicyclic group having the following structure:

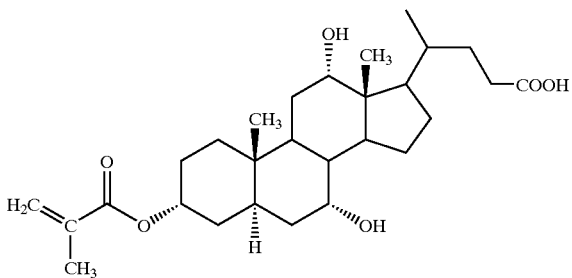

SUMMARY OF THE INVENTION

It is therefore an object of the present invention to provide a novel (meth)acrylic acid ester compound.

It is another object of the present invention to provide a novel (meth)acrylic acid ester compound useful as a resin material for photosensitive compositions, which enables control of the molecular weight of a resin to be prepared.

These and other objects of the present invention will become more apparent from the following detailed description and examples.

The inventors made extensive studies of solution to the foregoing difficulties. As a result, it was found that the foregoing objects of the present invention can be successfully accomplished by the following constitution. The present invention has been thus worked out.

The present invention has the following constitution:

A (meth)acrylic acid ester compound represented by the following general formula (I):

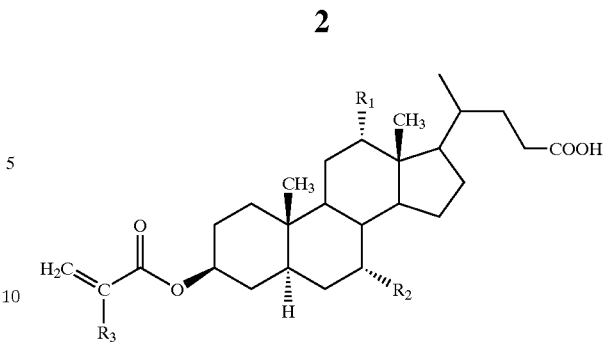

wherein $R_1$ and $R_2$ each independently represent a hydrogen atom or a hydroxyl group; and $R_3$ represents a hydrogen atom or a methyl group.

The (meth) acrylic acid ester compound represented by the general formula (I) of the present invention differs structurally from those described in the above cited Makromol. Chem., vol. 193, p. 779 (1992). That is, the (meth) acrylic acid ester compound represented by the general formula (I) of the present invention differs the conventional (meth)acrylic acid ester compounds in polycyclic structure and direction of bonding in ester moiety. It is thought that this structural difference governs the control over the polymerization reaction of these compounds.

The (meth) acrylic acid ester compound represented by the general formula (I) of the present invention is useful as a monomer component for a resin in a photosensitive resist component for use in the production of semiconductors such as IC and circuit board for liquid crystal, thermal head, etc., a monomer component for a resin to be incorporated in a photosensitive printing plate or a monomer component for a resin which can be preferably incorporated in a photosensitive composition for use in other photofabrication processes as mentioned above. In particular, the (meth) acrylic acid ester compound represented by the general formula (I) of the present invention can be preferably used as a monomer component for a resin to be used for photoresist composition for ArF exima laser exposure.

Thus, if the polymerization reaction of monomers cannot be controlled to synthesize a resin to be incorporated in a photosensitive composition, the resulting resin exhibits too great a molecular weight distribution. If such a resin is incorporated in a photosensitive composition, a portion having a high molecular weight may remain on the image developed as a residue to disadvantage.

The (meth)acrylic acid ester compound represented by the general formula (I) of the present invention causes no such a trouble.

DETAILED DESCRIPTION OF THE INVENTION

The compound of the present invention will be further described hereinafter.

The synthesis of the (meth)acrylic acid ester compound represented by the general formula (I) of the present invention can be accomplished by the following process.

In some detail, the synthesis reaction can be carried out by a process which comprises previously protecting the carboxylic acid site in bile acid (commercial product can be used) as a starting material, dissolving the bile acid thus protected in a solvent such as tetrahydrofuran (THF), adding excess triphenyl phosphine and excess acrylic acid or methacrylic acid to the solution, and then adding excess dialkyl azobiscarboxylate dropwise to the mixture at room temperature.

Examples of the solvent to be used herein include THF, dioxane, toluene, dichloromethane, and chloroform. These solvents may be used singly or in admixture.

The reaction may be effected at a temperature of from 0° C. to 40° C. If the reaction temperature falls below 0° C., the reaction rate is too low. Thus, the reaction takes much time to disadvantage. On the contrary, if the reaction temperature exceeds 40° C., the radical-polymerizable moiety can react or other side reactions cause the production of much by-products, which makes it difficult to purify the desired product and reduces the yield of the desired product.

The reaction time can be properly predetermined depending on the reaction temperature. In practice, however, it is preferably from 10 hours to 30 hours. As the alkyl in dialkyl azobiscarboxylate there can be used a commercially available product such as ethyl and isopropyl. The dialkyl azobiscarboxylate may be used in the form of solution.

The identification of the compound thus obtained can be carried out by NMR, optionally in combination with IR, GPC or elemental analysis.

The added amount of triphenyl phosphine, acrylic acid or methacrylic acid and dialkyl azobiscarboxylate each are preferably from 1.01 to 10 equivalents, more preferably from 1.1 to 4 equivalents, most preferably from 1.5 to 3 equivalents based on equivalent of bile acid. If the added amount of these components each fall below 1.01 equivalents, the reaction can difficultly proceed. On the contrary, if the added amount of these components each exceed 10 equivalents, a large amount of by-products may be produced, making it difficult to purify the desired product.

The synthesis of the methacrylic acid ester compound described in Makromol. Chem., vol. 193, p. 779 (1992) is carried out by a process which comprises previously protecting the carboxylic acid site in bile acid as a starting material, and then reacting the bile acid thus protected with methacylic acid chloride under the basic conditions such as the presence of triethylamine etc. In this reaction, the hydroxyl group in the molecule of bile acid makes nucleophilic attack on the carbonyl group in acid chloride. Thus, the steric configuration of the carbon atom in the 3-position of bile acid is retained. On the other hand, the synthesis of the compound of the present invention involves the nucleophilic attack of acrylic acid and methacrylic acid on the 3-position of bile acid. Thus, the carbon in the 3-position of bile acid is sterically inverted.

The (meth)acrylic acid ester compound of the present invention can be polymerized to obtain a resin by stirring and heating the (meth)acrylic acid ester compound singly or in combination with other copolymerizable monomers in the presence of a commercially available radical polymerization initiator such as azobisisobutyronitrile (AIBN). The resin can be used as an alkali-soluble resin. Furthermore, the resin can be protected with an acid-decomposable group and then used as an acid-decomposable resin. The introduction of the acid-decomposable group can be effected either before or after the polymerization.

The alkali-soluble resin can be used in combination with a photosensitive compound capable of generating an acid with irradiation of light such as naphthoquinone diazide sulfonate to provide a photosensitive composition, and can be used in combination with a photo-acid generator and an acid-decomposable compound obtained by protecting an alkali-soluble group with an acid-decomposable group to provide an acid-amplified type photosensitive composition. The acid-decomposable resin can be used in combination with a photo-acid generator to provide an acid-amplified type photosensitive composition.

These photosensitive compositions can be prepared by dissolving the respective constituting materials in a solvent.

EXAMPLES

The present invention will be further described in the following examples, but the present invention should not be construed as being limited thereto.

$R_1$, $R_2$ and $R_3$ are as defined in the general formula (I).

$^1$H-NMR was measured at 300 MHz in heavy chloroform as a solvent.

Synthesis Example 1
Synthesis of Compound 1 ($R_1$: OH; $R_2$: H; $R_3$: $CH_3$)

75 g of deoxycholic acid and 11 of dimethylformamide were charged in a 21 three-necked flask, and then stirred at room temperature to effect dissolution. To the solution was then added 19.2 g of triethylamine. To the mixture was then added dropwise ethoxymethyl chloride. After the termination of dropwise addition, the reaction mixture was stirred for 3 hours to terminate the reaction. After the termination of the reaction, the solvent was distilled off under reduced pressure. The residue was then extracted with an ethyl acetate/water system. The ethyl acetate solution thus obtained was dehydrated, and then re-concentrated to obtain 70 g of an ethoxymethyl-protected deoxycholic acid.

The protected deoxycholic acid thus obtained was dissolved in 21 of THF, and then charged into a 31 three-necked flask, along with 100 g of triphenyl phosphine. To the mixture was then added 33 g of methacrylic acid. To the mixture was then added dropwise 66 g of diethyl azobiscarboxylate. After the termination of dropwise addition, the mixture was stirred for 16 hours. The resulting reaction mixture was concentrated, and then extracted with a mixture of ethyl acetate and aqueous sodium bicarbonate. The resulting ethyl acetate phase was filtered, concentrated, and then dissolved in acetone. To the acetone solution was then added an aqueous solution of hydrochloric acid to cause hydrolysis. After the termination of the reaction, the reaction solution was neutralized, concentrated, and then purified by silica gel column chromatography to obtain 45 g of Compound 1 as the desired compound.

$^1$H-NMR (300 MHz, heavy chloroform):
6.10 ppm (1H, s), 5.53 ppm (1H, s), 5.14 ppm (1H, s), 4.00 ppm (1H, s), 2.36 ppm (2H, m), 1.94 ppm (3H, s), 1.00 ppm (3H, d), 0.97 ppm (3H, s), 0.70 ppm (3H, s) m.p.: 192–193° C.

Synthesis Example 2
Synthesis of Compound 2 ($R_1$: OH; $R_2$: H; $R_3$: H)

The reaction procedure of Synthesis Example 1 was followed except that 30 g of acrylic acid was used instead of methacrylic acid. As a result, 28 g of Compound 2 was obtained.

$^1$H-NMR (300 MHz, heavy chloroform):
6.39 ppm (1H, d), 6.12 ppm (1H, dd), 5.79 ppm (1H, d), 5.17 ppm (1H, s), 3.99 ppm (1H, s), 2.33 ppm (2H, m), 1.00 ppm (3H, d), 0.97 ppm (3H, s), 0.70 ppm (3H, s)
m.p.: 186–189° C.

Synthesis Example 3
Synthesis of Compound 3 ($R_1$: OH; $R_2$: OH; $R_3$: $CH_3$)

78 g of cholic acid and 11 of dimethylformamide were charged in a 21 three-necked flask, and then stirred at room temperature to effect dissolution. To the solution was then added 19.2 g of triethylamine. To the mixture was then added dropwise ethoxymethyl chloride. After the termination of dropwise addition, the reaction mixture was stirred for 3 hours to terminate the reaction. After the termination of the reaction, the solvent was distilled off under reduced pressure. The residue was then extracted with an ethyl acetate/water system. The ethyl acetate solution thus obtained was dehydrated, and then re-concentrated to obtain 72 g of an ethoxymethyl-protected cholic acid.

The protected cholic acid thus obtained was dissolved in 21 of THF, and then charged into a 31 three-necked flask, along with 100 g of triphenyl phosphine. To the mixture was then added 33 g of methacrylic acid. To the mixture was then added dropwise 66 g of diethyl azobiscarboxylate. After the termination of dropwise addition, the mixture was stirred for 16 hours. The resulting reaction mixture was concentrated, and then extracted with a mixture of ethyl acetate and aqueous sodium bicarbonate. The resulting ethyl acetate phase was filtered, concentrated, and then dissolved in acetone. To the acetone solution was then added an aqueous solution of hydrochloric acid to cause hydrolysis. After the termination of the reaction, the reaction solution was neutralized, concentrated, and then purified by silica gel column chromatography to obtain 48 g of Compound 3 as the desired compound.

$^1$H-NMR (300 MHz, heavy chloroform):
6.10 ppm (1H, s), 5.53 ppm (1H, s), 5.14 ppm (1H, s), 3.99 ppm (1H, s), 3.85 ppm (1H, s), 2.34 ppm (2H, m), 1.94 ppm (3H, s), 1.00 ppm (3H, d), 0.97 ppm (3H, s), 0.70 (3H, s)
m.p.: 222–224° C.

Synthesis Example 4
Synthesis of Compound 4 ($R_1$: OH; $R_2$: OH; $R_3$: H)

The reaction procedure of Synthesis Example 3 was followed except that 30 g of acrylic acid was used instead of methacrylic acid. As a result, 32 g of Compound 4 was obtained.

$^1$H-NMR (300 MHz, heavy chloroform):
6.39 ppm (1H, d), 6.12 ppm (1H, dd), 5.79 ppm (1H, d), 5.16 ppm (1H, s), 3.99 ppm (1H, s), 3.85 ppm (1H, s), 2.33 ppm (2H, m), 0.99 ppm (3H, d), 0.97 ppm (3H, s), 0.70 ppm (3H, s)
m.p.: 216–219° C.

Synthesis Example 5
Synthesis of Compound 5 ($R_1$: H; $R_2$: OH; $R_3$: $CH_3$)

75 g of chenocholic acid and 11 of dimethylformamide were charged in a 21 three-necked flask, and then stirred at room temperature to effect dissolution. To the solution was then added 19.2 g of triethylamine. To the mixture was then added dropwise ethoxymethyl chloride. After the termination of dropwise addition, the reaction mixture was stirred for 3 hours to terminate the reaction. After the termination of the reaction, the solvent was distilled off under reduced pressure. The residue was then extracted with an ethyl acetate/water system. The ethyl acetate solution thus obtained was dehydrated, and then re-concentrated to obtain 69 g of an ethoxymethyl-protected chenocholic acid.

The protected chenocholic acid thus obtained was dissolved in 21 of THF, and then charged into a 31 three-necked flask, along with 100 g of triphenyl phosphine. To the mixture was then added 33 g of methacrylic acid. To the mixture was then added dropwise 66 g of diethyl azobiscarboxylate. After the termination of dropwise addition, the mixture was stirred for 16 hours. The resulting reaction mixture was concentrated, and then extracted with a mixture of ethyl acetate and aqueous sodium bicarbonate. The resulting ethyl acetate phase was filtered, concentrated, and then dissolved in acetone. To the acetone solution was then added an aqueous solution of hydrochloric acid to cause hydrolysis. After the termination of the reaction, the reaction solution was neutralized, concentrated, and then purified by silica gel column chromatography to obtain 43 g of Compound 5 as the desired compound.

$^1$H-NMR (300 MHz, heavy chloroform):
6.10 ppm (1H, s), 5.53 ppm (1H, s), 5.14 ppm (1H, s), 3.86 ppm (1H, s), 2.35 ppm (2H, m), 1.94 ppm (3H, s), 1.00 ppm (3H, d), 0.97 ppm (3H, s), 0.70 ppm (3H, s)
m.p.: 191–194° C.

Synthesis Example 6
Synthesis of Compound 6 ($R_1$: H; $R_2$: OH; $R_3$: H)

The reaction procedure of Synthesis Example 5 was followed except that 30 g of acrylic acid was used instead of methacrylic acid. As a result, 30 g of Compound 6 was obtained.

$^1$H-NMR (300 MHz, heavy chloroform):
6.39 ppm (1H, d), 6.12 ppm (1H, dd), 5.79 ppm (1H, d), 5.16 ppm (1H, s), 3.86 ppm (1H, s), 2.33 ppm (2H, m), 0.99 ppm (3H, d), 0.96 ppm (3H, s), 0.70 ppm (3H, s)
m.p.: 187–190° C.

Synthesis Example 7
Synthesis of Compound 7 ($R_1$: H; $R_2$: H; $R_3$: $CH_3$)

72 g of lithocholic acid and 11 of dimethylformamide were charged in a 21 three-necked flask where they were then stirred at room temperature to make a solution. To the solution was then added 19.2 g of triethylamine. To the mixture was then added dropwise ethoxymethyl chloride. After the termination of dropwise addition, the reaction mixture was stirred for 3 hours to terminate the reaction. After the termination of the reaction, the solvent was distilled off under reduced pressure. The residue was then extracted with an ethyl acetate/water system. The ethyl acetate solution thus obtained was dehydrated, and then re-concentrated to obtain 65 g of an ethoxymethyl-protected lithocholic acid.

The protected lithocholic acid thus obtained was dissolved in 21 of THF, and then charged into a 31 three-necked flask, along with 100 g of triphenyl phosphine. To the mixture was then added 33 g of methacrylic acid. To the mixture was then added dropwise 66 g of diethyl azobiscarboxylate. After the termination of dropwise addition, the mixture was stirred for 16 hours. The resulting reaction mixture was concentrated, and then extracted with a mixture of ethyl acetate and aqueous sodium bicarbonate. The resulting ethyl acetate phase was filtered, concentrated, and then dissolved in acetone. To the acetone solution was then added an aqueous solution of hydrochloric acid to cause hydrolysis. After the termination of the reaction, the reaction solution was neutralized, concentrated, and then purified by silica gel column chromatography to obtain 42 g of Compound 7 as the desired compound.

$^1$H-NMR (300 MHz, heavy chloroform):
6.10 ppm (1H, s), 5.53 ppm (1H, s), 5.14 ppm (1H, s), 2.33 ppm (2H, m), 1.94 ppm (3H, s), 1.00 ppm (3H, d), 0.97 ppm (3H, s), 0.70 ppm (3H, s)
m.p.: 152–155° C.

Synthesis Example 8
Synthesis of Compound 8 ($R_1$: H; $R_2$: H; $R_3$: H)

The reaction procedure of Synthesis Example 7 was followed except that 30 g of acrylic acid was used instead of methacrylic acid. As a result, 35 g of Compound 8 was obtained.

$^1$H-NMR (300 MHz, heavy chloroform):
6.39 ppm (1H, d), 6.12 ppm (1H, dd), 5.79 ppm (1H, d), 5.17 ppm (1H, s), 2.33 ppm (2H, m), 0.99 ppm (3H, d), 0.97 ppm (3H, s), 0.71 ppm (3H, s)
m.p.: 147–150° C.

In accordance with the present invention, the molecular weight of the resin thus obtained can be controlled, making it possible to provide a novel (meth)acrylic acid ester compound useful as a monomer material for resin to be incorporated in a photosensitive composition.

While the invention has been described in detail and with reference to specific embodiments thereof, it will be apparent to one skilled in the art that various changes and modifications can be made therein without departing from the spirit and scope thereof.

What is claimed is:

1. A polymerizable (meth)acrylic acid ester compound for an alkali-soluble resin represented by the following general formula (I):

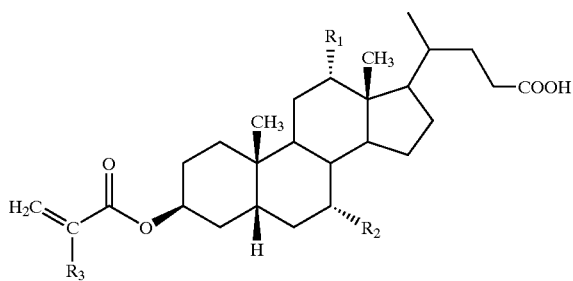

wherein $R_1$ and $R_2$ each independently represents a hydrogen atom or a hydroxyl group, and $R_3$ represents a hydrogen atom or a methyl group, provided that $R_3$ represents a hydrogen atom when $R_1$ and $R_2$ each represents a hydroxyl group.

2. The polymerizable (meth)acrylic acid ester compound for an alkali-soluble resin of claim 1, wherein $R_1$ represents a hydroxyl group, $R_2$ represents a hydrogen atom, and $R_3$ represents a methyl group.

3. The polymerizable (meth)acrylic acid ester compound for an alkali-soluble resin of claim 1, wherein $R_1$ represents a hydroxyl group, $R_2$ represents a hydrogen atom, and $R_3$ represents a hydrogen atom.

4. The polymerizable (meth)acrylic acid ester compound for an alkali-soluble resin of claim 1, wherein $R_1$ represents a hydroxyl group, $R_2$ represents a hydroxyl group and $R_3$ represents a hydrogen atom.

5. The polymerizable (meth)acrylic acid ester compound for an alkali-soluble resin of claim 1, wherein $R_1$ represents a hydrogen atom, $R_2$ represents a hydrogen atom, and $R_3$ represents a methyl group.

6. The polymerizable (meth)acrylic acid ester compound for an alkali-soluble resin of claim 1, wherein $R_1$ represents a hydrogen atom, $R_2$ represents a hydrogen atom, and $R_3$ represents a hydrogen atom.

7. The polymerizable (meth)acrylic acid ester compound for an alkali-soluble resin of claim 1, wherein $R_1$ represents a hydrogen atom, $R_2$ represents a hydroxyl group, and $R_3$ represents a methyl group.

8. The polymerizable (meth)acrylic acid ester compound for an alkali-soluble resin of claim 1, wherein $R_1$ represents a hydrogen atom, $R_2$ represents a hydroxyl group, and $R_3$ represents a hydrogen atom.

* * * * *